United States Patent [19]

Ikada et al.

[11] Patent Number: 4,743,258

[45] Date of Patent: May 10, 1988

[54] POLYMER MATERIALS FOR VASCULAR PROSTHESES

[75] Inventors: Yoshito Ikada; Hiroo Iwata, both of Uji; Masakazu Suzuki, Kyoto, all of Japan

[73] Assignees: Japan Medical Supply Co., Ltd., Hiroshima; Yoshito Ikada, Uji, both of Japan

[21] Appl. No.: 722,669

[22] Filed: Apr. 12, 1985

[30] Foreign Application Priority Data

Apr. 27, 1984 [JP] Japan ................... 59-87432

[51] Int. Cl.$^4$ ............ A61F 2/02; A61F 2/54
[52] U.S. Cl. ............................... 623/1; 623/11; 623/66; 427/2; 427/255.6; 428/289; 428/341
[58] Field of Search ............. 3/1, 1.4; 427/2, 41, 427/40, 255.6, 35, 39; 128/334 R; 623/1, 12, 66 A, 66 C, 2; 428/289, 341

[56] References Cited

U.S. PATENT DOCUMENTS

| | | | |
|---|---|---|---|
| 3,730,753 | 5/1973 | Kerr | 427/35 |
| 3,969,130 | 7/1976 | Bokros | 623/2 |
| 4,008,047 | 2/1977 | Petersen | 128/DIG. 3 |
| 4,143,949 | 3/1979 | Chen | 427/41 |
| 4,167,045 | 9/1979 | Sawyer | 427/2 |
| 4,193,138 | 3/1980 | Okita | 623/1 |
| 4,326,305 | 4/1982 | Davidas | 427/2 |
| 4,377,010 | 3/1983 | Fydelor et al. | 3/1 |
| 4,378,803 | 4/1983 | Jakagi et al. | 623/66 |
| 4,387,183 | 6/1983 | Francis | 427/2 |
| 4,482,577 | 11/1984 | Goldstein et al. | 427/2 |
| 4,634,599 | 1/1987 | Vzgiris | 427/2 |
| 4,666,437 | 5/1987 | Lambert | 427/2 |
| 4,670,313 | 6/1987 | Saudagar | 604/53 |

FOREIGN PATENT DOCUMENTS

| | | | |
|---|---|---|---|
| 42759 | 12/1971 | Japan . | |
| 66187 | 9/1973 | Japan . | |
| 125493 | 11/1974 | Japan . | |
| 150793 | 12/1975 | Japan . | |
| 24651 | 2/1976 | Japan . | |
| 125978 | 11/1976 | Japan . | |
| 106778 | 2/1977 | Japan . | |
| 0069985 | 6/1977 | Japan | 427/40 |

OTHER PUBLICATIONS

*Polymors in Medicine;* Ed: Chiellini et al.; Author:-Jansen; pp. 287–295; 1983, Plenum Press, N.Y., N.Y.
S. W. Kim, E. S. Lee, J. Polym. Sci., Polym. Symposia, vol. 66, pp. 429–441 (1979).

*Primary Examiner*—Richard J. Apley
*Assistant Examiner*—Paul Prebilic
*Attorney, Agent, or Firm*—Kramer, Brufsky & Cifelli

[57] ABSTRACT

A highly blood-compatible material comprising a polymeric base material and water-soluble and substantially nonionic polymer(s) directly attached to the surface of the base material in an amount of 1 to 100 $\mu g/cm^2$. The polymeric base material is preferably in the form of a web and composed of polyurethane, ethylene/vinyl acetate copolymer or polyvinylchloride. In addition, the attached polymers may be selected from the group consisting of acrylamide polymers, polyvinylpyrrolidone, polyvinyl alcohol, polyethylene glycol, and dextran. This material is particularly useful for preparing vascular prosthesis of small diameters.

7 Claims, No Drawings

POLYMER MATERIALS FOR VASCULAR PROSTHESES

BACKGROUND OF THE INVENTION

This invention relates to a material which exhibits excellent blood compatibility. More particularly, it relates to a blood-compatible material suitable for small-diameter vascular prostheses.

Vascular prostheses are examples of materials which must be compatible with blood. However, vascular prostheses currently available are prepared from polyester knitted web or porous polytetrafluoroethylene and exhibit insufficient blood compatibility, so that they are usable only for arteries of a large diameter wherein thrombotic occlusion rarely occurs. When these vascular prostheses are employed for arteries of a small diameter or for veins, thrombosis and resultant occlusion often would occur within a short period of time.

Various materials having improved blood compatibility have been proposed as will be described hereinafter. However, each of them is somewhwat unsuitable for use in vascular prostheses of small diameter. In Japanese Patent Publication No. 42759/1971 and Japanese Patent Laid-Open Nos. 150793/1975 and 24651/1976, blood-compatible materials which are prepared from hydrogel obtained by crosslinking hydrophilic polymers such as poly(2-hydroxyethyl methacrylate) and polyvinyl alcohol are disclosed. However, these materials cannot be applied to vascular prostheses because of their insufficient blood compatibility and low strength. Japanese Patent Laid-Open Nos. 125493/1974 and 125978/1976 disclose processes for improving blood compatibility by graft polymerizing the above mentioned hydrophilic polymer(s) onto the surface of a base material. The blood-compatible material which is prepared according to the foregoing processes with the use of an appropriate base material would exhibit satisfactory tensile strength. However, the blood compatibility thereof is similar to those of the hydrophilic polymers. Therefore thrombosis and resulting occlusion would occur within a short period of time if this material were used for vascular prostheses of small diameter.

In addition, Japanese Patent Laid-Open Nos. 66187/1973 and 106778/1978 disclose processes for imparting blood compatibility by fixing anticoagulants such as heparin or urokinase onto the surface of certain materials. The blood compatibility of a material thus obtained is high at the beginning but gradually decreases so that it is impossible to obtain a stable, satisfactory blood compatibility level. This instability may be caused by a decrease in the anticoagulant effect resulting from gradual denaturation of the anticoagulants fixed on the surface of the material. These processes have another disadvantage in the high cost of the anticoagulants themselves as well as the expense required for the fixing treatment.

Thus, despite the numerous proposals as described above, no material which exhibits excellent blood compatibility for a long period of time is available for vascular prostheses of small diameter.

SUMMARY OF THE INVENTION

It is an object of the present invention to provide a material which has excellent blood compatibility and can be used in vascular prostheses of small diameter. It is another object of the present invention to provide a material on which there is hardly any adsorption of protein.

The aforementioned objects can be achieved by attaching 1 to 100 $\mu g/cm^2$, preferably 10 to 50 $\mu g/cm^2$, of water-soluble and substantially nonionic polymer(s) onto the surface of a polymeric base material.

DETAILED DESCRIPTION OF THE INVENTION

The term "water-soluble and substantially nonionic polymer(s)" as used herein means those which are soluble in water as a single polymer and have no or few ionic groups. Water-soluble polymers having many ionic groups cannot be employed since they exhibit poor blood compatibility. Examples of preferred polymers are: acrylamide polymers such as polyacrylamide and polydimethylacrylamide; methacrylamide polymers such as polymethylacrylamide; polyvinylpyrrolidone; partially or completely saponified polyvinyl alcohol; polyethylene glycol; and dextran. For blood compatibility, polyacrylamide polymers, polyvinylpyrrolidone and polyvinyl alcohol are particularly preferred. One or more of these polymers may be employed. The polymers may be either homopolymers or copolymers. As described above, the polymer(s) used in the present invention should be water-soluble. However, they need not necessarily be water-soluble at normal temperature and those soluble in water at elevated temperatures are also available.

The water-soluble and substantially nonionic polymer(s) should be attached onto the surface of a polymeric base material at a ratio of 1 to 100 $\mu g/cm^2$, which is significantly lower than the amount of hydrophilic polymers used in the conventional graft polymerization. The conventional graft polymerization is based on recognition that a base material coated with hydrophilic polymers would exhibit blood compatibility similar to those of the hydrophilic polymers. Thus approximately 10 to 100 $mg/cm^2$ of hydrophilic polymers are subjected to graft polymerization to thereby completely coat the surface of the base material. Accordingly, the graft polymerization results in an increase in the weight of the sample by approximately 1 to 20%. On the contrary, the water-soluble polymer layer in the process of the present invention is so thin that it hardly brings about any increase in the weight. Thus, it has been unexpectedly found that higher blood compatibility would be obtained by attaching a smaller amount of polymer(s). It is particularly preferred to attach 1 to 50 $\mu g/cm^2$ of polymer(s).

The water-soluble and substantially nonionic polymer(s) may be attached onto the surface of a base material in a manner well-known in the art under the conditions selected to allow the polymer(s) to be attached in the ratio as determined above. The attachment may be carried out by, for example, (A) forming radicals or peroxides on the surface of a base material and contacting monomer(s) therewith, thus effecting graft polymerization; or (B) previously forming polymer(s) and chemically attaching them onto the surface of the base material by taking advantage of reactive groups thereof. Said radicals or peroxides may be formed by (1) irradiating with high-energy radiation such as electron beam or $\gamma$-ray; (2) irradiating with UV light; (3) low-temperature plasma discharge; (4) corona discharge; (5) ozone treatment; and (6) adding a radical polymerization initiator such as benzoyl peroxide. Polymerization may be carried out by adding monomer(s) simultaneously with the base material to be treated at the treatment step or contacting the treated base material with the monomer(s). The amount of the polymer(s) to be attached may be adjusted by controlling various factors such as the condition under which the base material is treated, the period of contact with the monomer(s) and temperature. Examples of available monomers are acrylamide, dimethylacrylamide, methacrylamide, vinylpyrrolidone, vinyl acetate and ethylene oxide. Vinyl acetate may be converted into polyvinyl alcohol by saponifying after the polymerization.

Polymer(s) previously prepared may be attached onto the surface of a base material either by directly reacting reactive group(s) on the surface of the base material with that of the polymer(s) or via certain specific compounds. The latter method is suitable for polymers having hydroxyl group(s) in the molecule, such as polyvinyl alcohol, polyethylene glycol and dextran. These polymers may be preferably attached to the base material having hydroxyl group(s) via a diisocyanate compound.

A wide range of base materials may be used in the present invention; the particular polymeric materials may be used depending on the aimed purpose and usage. Examples of the polymeric material are polyethylene, ethylene/vinyl acetate copolymer optionally saponified partially or completely, polypropylene, propylene copolymer, polyvinyl chloride, polyvinylidene chloride, polystyrene, polyacrylonitrile, polymethyl methacrylate, styrene/butadiene block copolymers, acrylonitrile/butadiene/styrene block copolymers, polybutadiene, polyisoprene, polytetrafluoroethylene, polyethylene terephthalate, polyethylene isophthalate, polybutylene terephthalate, polyether/ester block copolymers, polycarbonate, nylon 6, nylon 66, nylon 12, polyurethane, polysulfone, polyether sulfone, silicone resin, silicone rubber and cellulose and derivatives thereof, and the like. When radicals or peroxides are formed on the surface of the base material to effect graft polymerization, these materials may be used without limitation. On the other hand, when polymer(s) are chemically attached onto the surface of the base material, ethylene/vinyl acetate copolymer optionally saponified partially or completely are preferably used since they have reactive groups on the surface.

The base material may be in any form such as nonporous, porous, fabric or knitted web depending on the purpose. It may also be in any shape such as a tube, a sheet, a plate, a block or fibers. Either a material comprising a single component or a compound material comprising a plurality of components may be used. Water-soluble polymer(s) may be attached onto the whole surface of the base material. Alternatively, they may be selectively attached to a particular part in contact with blood.

The material of the present invention has excellent blood compatibility and is suitable for vascular prostheses, in particular those having internal diameters of several mm or below. It is further available for other instruments and devices in direct contact with blood, such as an intravascular catheter, artificial heart, lung, kidney and liver and blood circuit. It is furthermore available for instruments for transfusion and hematometry since blood cells and platelets would hardly adhere thereto.

The material of the present invention is advantageous in that it may be prepared readily and inexpensively by chemically treating the base material. The non-limited shape thereof makes it available in various ways. Furthermore, it may be readily sterilized with steam or ethylene oxide without lowering the blood compatibility, thus increasing safety in application.

In the process of the present invention, it is essential to adjust the amount of the water-soluble and substantially nonionic polymer(s) to be attached so that is is within the aforementioned range. The amount of the attached polymer(s) may be determined by, e.g., the following methods.

(1) A sample is chemically treated to liberate a part or the whole of the attached polymer(s) to determine the liberated matter.

(2) A sample is dissolved in a solvent in which the base material is soluble but the water-soluble polymer(s) are insoluble in order to separate the water-soluble polymer(s), then the amount of polymer(s) is determined.

(3) The monomer(s) or polymer(s) to be used is previously labelled with a radioisotope and the radioactivity of the sample is determined after attachment to the base material.

(4) The amount of the attached polymer(s) is determined by attenuated total reflection infrared spectroscopy (ATR-IR) with the use of calibration curves which have been previously determined.

An appropriate method for determination may be selected depending on the base material and the attached polymer(s).

The following specific examples are furnished in order to illustrate the invention. They constitute exemplification only and are not to be regarded as limitations.

EXAMPLE 1

A high-density polyethylene film of 60 $\mu$m in thickness was cleaned by extraction with ethanol and irradiated with $^{60}$Co $\gamma$-ray at a dose rate of 0.02 Mrad/hr to a dose of 1.5 Mrad in dry air. The irradiated film was stored in a desiccator for two days after the irradiation at room temperature. Then it was immersed in an aqueous solution containing 25% by weight of acrylamide and $5\times10^{-4}$ mol/liter of $FeSO_4$ in a test tube. After deaeration, the tube was sealed and allowed to stand in a thermostatic water bath at 15° C. to thereby carry out graft polymerization. After 25 hours, the tube was opened and homopolymer adhering to the surface of the film was removed by washing with water, thereby yielding a polyethylene film having polyacrylamide attached thereon.

The amount of the attached polyacrylamide in the sample thus obtained was determined in the following manner. The sample was immersed in 1.5N HCl and treated in an autoclave at 2.5 atm for 30 min to hydrolyze the polyacrylamide. Then it was neutralized with NaOH and a ninhydrin solution was added thereto. After reacting in an autoclave at 3 atm for five min, the absorbance of the reaction mixture was determined at 570 nm. The amount of the attached polyacrylamide was calculated by the determined value and a calibration curve which had been previously determined. The process for determining the attached polymer(s) in the above manner will be referred to as "ninhydrin method" hereinbelow.

The amount of the attached polyacrylamide in the foregoing sample as determined by this method was 12 $\mu$g/cm$^2$. On the other hand, the amount of the attached polyacrylamide in a sample treated in the same manner except that it was not irradiated with $\gamma$-ray was zero within the range of allowable errors. No difference between the surfaces of the treated and untreated films was observed under a scanning electron microscope. The surface of the treated film was neutralized with NaOH and stained with toluidine blue. Optical microscopic observation of a section thereof revealed the localization of polyacrylamide on the surface of the film.

EXAMPLE 2

A commercially available polypropylene film of 50 μm in thickness was cleaned with methanol and subjected to corona discharge at atmospheric pressure in dry air. Two circular plates of stainless steel ($\phi$ 7.5 cm) were employed as electrodes and placed at a distance of 5.5 mm. Each electrode was covered with a glass plate of 2 mm in thickness. Slide glass plates were inserted as a spacer and the sample was placed therein. The discharge was conducted at a frequency of 60 Hz and at an applied volage of 9 kV for 30 sec. The corona discharge treated film was then immmersed in an aqueous solution containing 20% by weight of vinylpyrrolidone. After removing dissolved air, the solution was heated to 70° C. for three hours to accelerate graft polymerization of the vinylpyrrolidone. After removing homopolymer, the obtained product was dried and the amount of the attached polyvinylpyrrolidone was determined by infrared absorption with the guidance of the absorption wave number of carbonyl group at 1670 $cm^{-1}$. Consequently it was found that the amount of the polyvinylpyrrolidone attached to the polypropylene film was 15 $\mu g/cm^2$. The contact angles of the surfaces of the treated and untreated films to water were 35° and 90°, respectively.

EXAMPLE 3

A sheet of 0.1 mm in thickness was prepared from ethylene/vinyl acetate copolymer (EVA) containing 10% by weight of vinyl acetate by hot-pressing. The sheet was cleaned with ethanol and treated with argon gas plasma by a low-temperature plasma surface treatment apparatus at an output of 11.5 W, at a gas flow rate of 20 $cm^3$/min and at 0.04 Torr for 30 sec. The plasma-pretreated EVA sheet was then taken out and stored in a desiccator. The sheet was immersed in an aqueous solution containing 10% by weight of acrylamide and the air dissolved in the aqueous solution was replaced with nitrogen gas thereby carrying out graft polymerization at 50° C. for two hours. The amount of the attached polyacrylamide determined by the ninhydrin method was 18 $\mu g/cm^2$. Optical microscopic observation of a stained section of the film revealed that the graft polymerization proceeded to a depth of approximately 0.2 μm from the surface.

EXAMPLE 4

(Comparative Example 1)

The insides of a polyether urethane tube and a low-density polyethylene tube, each of 3 mm in internal diameter and 3.5 mm in external diameter, were subjected to corona discharge under various conditions and then polyacrylamide was graft polymerized thereto, thus obtaining tubes to which various amounts of polyacrylamide were attached. In order to examine the blood compatibility of these samples, adsorption of serum protein on the inside of the tubes was examined. Bovine serum albumin (BSA) and immuno-gamma-globulin (IgG) were fluorescently labelled with fluorescein isothiocyanate (FITC). These labelled materials were mixed respectively with non-labelled BSA and IgG to give aqueous protein solutions each containing 2 mg/ml of protein in total. The sample tubes as prepared above were immersed in these aqueous solutions at 37° C. for three hours to allow the adsorption of the protein. Then the surfaces of the tubes were slowly washed with a buffer solution to remove unadsorbed protein. Subsequently the adsorbed protein was hydrolyzed in an autoclave at 3 atm for one hour. The fluorescence intensity of the FITC was determined at an excitation wavelength of 490 nm and a fluorescence wavelength of 520 nm. The amount of the adsorbed protein was determined by the measured values and calibration curves which had been previously determined. Table 1 shows the result.

TABLE 1

| Amount of Adsorbed Protein | | | |
|---|---|---|---|
| | Attached Polyacrylamide ($\mu g/cm^2$) | Adsorbed Protein ($\mu g/cm^2$) | |
| | | BSA | IgG |
| Polyethylene tube | 0 | 0.3 | 0.9 |
| | 12 | 0.1 | 0.2 |
| | 30 | 0.05 | 0.1 |
| | 120 | 0.3 | 0.4 |
| | 330 | 2.0 | 1.5 |
| Polyurethane tube | 0 | 0.2 | 0.8 |
| | 5 | 0.15 | 0.4 |
| | 20 | 0.05 | 0.2 |
| | 45 | 0.10 | 0.3 |
| | 250 | 0.4 | 0.6 |
| | 500 | 1.2 | 1.4 |

Table 1 suggests that large amounts of protein would be adsorbed by untreated tubes and those to which more than 100 $\mu g/cm^2$ of acrylamide is attached, while the amounts of the protein adsorbed by those to which 1 to 100 $\mu g/cm^2$, in particular 10 to 50 $\mu g/cm^2$, of polyacrylamide is attached are smaller. It is well known that the blood compatibility of a polymeric surface would increase with a decrease in the amount of protein, in particular glucoprotein such as IgG, adsorbed thereby (cf. S. W. Kim, E. S. Lee, *J. Polym. Sci., Polym. Symposia*, vol. 66, pp. 429-441 (1979)). Therefore, the result as shown above suggests that the material of the present invention has excellent blood compatibility.

EXAMPLE 5

(Comparative Example 2)

A film of ethylene/vinyl alcohol copolymer containing 30 molar percent of ethylene of 50 μm in thickness was subjected to glow discharge. Acrylamide, dimethylacrylamide, acrylamido-2-methylpropane sulfonic acid (AMPS) and dimethylaminoethyl methacrylate (DMAEM) were independently graft polymerized thereto to give films to which 30 to 40 $\mu g/cm^2$ of polymers were attached.

0.1 ml portions of platelet-rich plasma from which calcium ions had been removed were poured onto these treated films and an untreated film to examine the adhesiveness of the platelets in a conventional manner. Consequently it was found that numerous platelets adhered to the untreated film while none adhered to those to which polyacrylamide and polydimethylacrylamide were graft polymerized. On the other hand, a large number of platelets adhered to those to which anionic polyAMPS and cationic polyDMAEM were graft polymerized, some of which showed pseudopodia.

The result as mentioned above suggests that the attachment of water-soluble and ionic polymers would result in poor blood compatibility.

EXAMPLE 6

The same film of ethylene/vinyl alcohol copolymer as used in Example 5 was treated with hexamethylene diisocyanate in toluene in the presence of dibutyltin dilaurate as a catalyst to react the hydroxyl group on the surface of the film with one of the isocyanate groups of the hexamethylene diisocyanate, thereby attaching the hexamethylene diisocyanate and introducing the isocyanate group onto the surface of the film. Dextran of a degree of polymerization of 600 and polyvinyl alcohol of a degree of polymerization of 1700 were independently attached thereto by a urethane coupling reaction to give films to which 30 $\mu$g/cm$^2$ and 20 $\mu$g/cm$^2$ of polymers were attached.

The obtained films were subjected to the same test as shown in Example 5 to examine the adhesiveness of platelets. It was found that no platelet adhered to either film.

EXAMPLE 7

(Comparative Example 3)

A low-density polyethylene tube of 1 mm in internal diameter and 1.3 mm in external diameter was cut into pieces of a length of 1.5 cm and the pieces were irradiated with electron beams in air at room temperature with the use of a Van De Graaff accelerator at an energy level of 1.5 MeV and at a dose rate of 0.1 Mrad/sec for 30, 70 and 300 sec, thereby preparing three types of samples. These samples were immersed in an aqueous solution containing $8 \times 10^{-5}$ mol/liter of FeSO$_4$ and 20% by weight of acrylamide at 15° C. for five hours for graft polymerization to thereby give samples to which 16 $\mu$g/cm$^2$, 33 $\mu$g/cm$^2$ or 150 $\mu$g/cm$^2$ of polyacrylamide were attached. A sample irradiated for 70 sec was immersed in an aqueous solution containing $8 \times 10^{-5}$ mol/liter of FeSO$_4$ and 20% by weight of acrylic acid at 15° C. for five hours for graft polymerization thereby giving a sample to which 22 $\mu$g/cm$^2$ of polyacrylic acid was attached.

These tubes and an untreated tube were implanted into the common carotid arteries of rats in the following manner. A rat was incised at the cervix to expose the common carotid artery. Approximately 1 cm of the artery was removed and substituted by the tube. Isobutyl cyanoacrylate was applied to the tube to effect anastomosis. After the completion of the anastomosis, blood was allowed to flow again and the artery was observed externally. In the case of the untreated tube, occlusion caused by thrombosis was observed within 5 min. and blood stopped flowing. In the case of the sample to which 22 $\mu$g/cm$^2$ of polyacrylic acid was attached, occlusion was also observed within 10 min. On the contrary, blood continued to flow without any occlusion at least for two hours in the case of the samples to which 16 $\mu$g/cm$^2$ or 33 $\mu$g/cm$^2$ of polyacrylamide was attached. In the case of the sample to which 150 $\mu$g/cm$^2$ of polyacrylamide was attached, occlusion was observed after one hour and 30 min.

EXAMPLE 8

(Comparative Example 4)

A polyurethane tube of 3 mm in internal diameter and 3.5 mm in external diameter was formed by coating a bar of low-density polyethylene with a solution of 7% polyether urethane of an Hs hardness of 80 in dimethylformamide and then removing the bar. The obtained tube was immersed in methanol for a long time to remove dimethylformamide and subjected to corona discharge at 10 kV for one min. Acrylamide was immediately graft polymerized to the tube for two and six hours to give tubes to which 22 $\mu$g/cm$^2$ and 150 $\mu$/cm$^2$ of polyacrylamide was attached, respectively. After removing homopolymer, the tubes were stored in a physiological saline solution. The cartoid artery of a mongrel dog was removed at a length of 3 cm and 3.5 cm of the polyurethane tube was inserted therein and anastomosed.

Blood was allowed to flow again and the artery was observed by naked eyes. In the case of the untreated tube, occlusion was observed within three hours. On the other hand, blood continued to flow for 20 hours in the case of the polyurethane tube to which 22 $\mu$g/cm$^2$ of polyacrylamide was attached, while occlusion was observed after six hours in the case of the tube to which 150 $\mu$g/cm$^2$ of polyacrylamide was attached.

What is claimed is:

1. A material for vascular prostheses which comprises a polymeric web as a base material and one or more water-soluble and substantially nonionic polymers attached to the surface by graft polymerization or chemical reaction with a reactive group of said surface of said base material in an amount of from 1 to 100 $\mu$g/cm$^2$, whereby IgG protein adsorbed to the surface is less than 0.4 $\mu$g/cm$^2$.

2. A material according to claim 1 wherein said polymeric web is prepared from a polymer selected from the group consisting of polyurethane, ethylene/vinyl acetate copolymer and polyvinyl chloride.

3. A material according to claim 1, wherein said polymers are attached in an amount of 1 to 50 $\mu$g/cm$^2$.

4. A material according to claim 1, wherein said polymers are selected from the group consisting of polyacrylamide, polydimethylacrylamide, polymethacrylamide, polyvinylpyrrolidone, polyvinyl alcohol, polyethylene glycol and dextran.

5. A material according to claim 4, wherein said polymers are selected from the group consisting of polyacrylamide, polyvinylpyrrolidone and polyvinyl alcohol.

6. A material according to claim 1, wherein said base material is porous.

7. A material according to claim 1, wherein said base material is in the form of a tube.

* * * * *